United States Patent
LeGrow et al.

(10) Patent No.: US 6,258,365 B1
(45) Date of Patent: *Jul. 10, 2001

(54) ORGANOSILICONE GEL COMPOSITIONS FOR PERSONAL CARE

(75) Inventors: Gary E. LeGrow, Newberry; W. Leonard Terry, Jr., Gainesville, both of FL (US)

(73) Assignee: Archimica (Florida), Inc., Gainesville, FL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/149,964

(22) Filed: Sep. 9, 1998

(51) Int. Cl.[7] ........................................ A61K 9/00
(52) U.S. Cl. .................... 424/400; 424/65; 424/70.12; 424/78.03; 514/944; 524/860
(58) Field of Search ................ 424/65, 400, 70.12, 424/78.03; 514/944; 524/860

(56) References Cited

U.S. PATENT DOCUMENTS

| | | | |
|---|---|---|---|
| 5,225,188 | * 7/1993 | Abrutyn et al. | 424/66 |
| 5,306,797 | 4/1994 | Ikeno | 528/15 |
| 5,336,497 | 8/1994 | Guerrero et al. | 424/401 |
| 5,413,781 | * 5/1995 | Giwa-Agbomeirele et al. | 424/78.03 |
| 5,623,017 | 4/1997 | Hill | 524/860 |
| 5,679,734 | 10/1997 | Peccoux et al. | 424/267 |
| 5,750,098 | * 5/1998 | Legrow et al. | 424/70.12 |
| 5,759,529 | 6/1998 | Legrow | 424/70 |

OTHER PUBLICATIONS

SEHSC, D4 (Octamethylcyclotetrasiloxane) Scientific Paper For Use By Member Companies, Jul. 20, 1998.

Dow Corning AMS–C30 Wax, advertisement, 1997.

* cited by examiner

Primary Examiner—Thurman K. Page
Assistant Examiner—Lakshmi Channavajjala
(74) Attorney, Agent, or Firm—Hedman & Costigan, P.C

(57) ABSTRACT

The present invention relates to compositions comprising non-toxic and safe for human contact and ingestion volatile or non-volatile silicone-aliphatic hydrocarbon hybrid fluids and a non-volatile silicone-aliphatic hydrocarbon hybrid wax which have the physical consistency of a gel which are of use in a wide variety of personal care applications and when applied to the human skin components within these compositions adsorb quickly into the upper layers of the status corneum, while other components form non-tacky occlusive films on the outer surface of the stratum corneum.

13 Claims, 2 Drawing Sheets

US 6,258,365 B1

ORGANOSILICONE GEL COMPOSITIONS FOR PERSONAL CARE

FIELD OF THE INVENTION

The present invention relates to compositions for use in personal care products. More particularly, the present invention relates to compositions for use in personal care products which have the physical form of a gel. Most particularly, the present invention relates to compositions for use in personal care products which when applied to the human skin, have component(s) which adsorb quickly into the upper layers of the status corneum, and have component(s) which form non-tacky occlusive films on the outer surface of the stratum corneum. Significantly, all of the components employed in the use of the compositions of the present invention are safe for human contact and ingestion.

BACKGROUND OF THE PRESENT INVENTION

It is well known in the art that an organosilicone gum can be used to thicken a cosmetic formulation containing organic components and organosilicone components such as dimethylcyclo-siloxanes and low molecular weight polydimethylsiloxanes. More recently, new silicone technologies have been found to thicken cosmetic formulations including silicone copolyols and their derivatives (U. S. Pat. Nos. 5,623,017 and 5,336,497), and lightly crosslinked silicone hydrosilylation addition compositions (U.S. Pat. Nos. 5,679,734 and 5,306,797). Thickening of cosmetic formulations is typically performed to minimize the product running on or from the surface to which it is applied.

It is also well known in the art that polydimethylsiloxanes, including gums and elastomeric materials, have a larger free volume than typical organic materials, thereby allowing water and other vapors to pass through them as readily as they pass through air. Consequently formulations containing silicone gums and elastomers generally do not form occlusive barriers on the skin. It is also well known in the art that polydimethylsiloxanes, including gums and elastomers, are not compatible with most organic materials used in personal care formulations, thereby making the development of homogeneous formulations with these ingredients difficult.

New information has recently been published about toxicity characteristics of octamethylcyclotetrasiloxane which is a common silicone component of many cosmetic formulations. See, SEHSC Report entitled "D4 (Octamethylcyclotetrasiloxane) Scientific Paper for Use by Member Companies" dated Jul. 20, 1998. This information would suggest that non-toxic alternatives to the use of this material would be desirable, and preferred.

The inclusion of a volatile alkylmethylsiloxane in a formulation with octamethylcyclotetrasiloxane and a polydimethylsiloxane gum has recently been described in U.S. Pat. No. 5,759,529 for the purpose of enhancing the rate of adsorption, and improving general aesthetic characteristics.

It would therefore represent a significant advance in the state of the art if a siloxane formulation could be provided which employed nontoxic silicone components in combination with a gelling agent which had improved compatibility characteristics with other cosmetic ingredient constituents, and which had substantially equivalent sensory characteristics to current siloxane cosmetic formulations.

SUMMARY OF THE INVENTION

Figure 1:
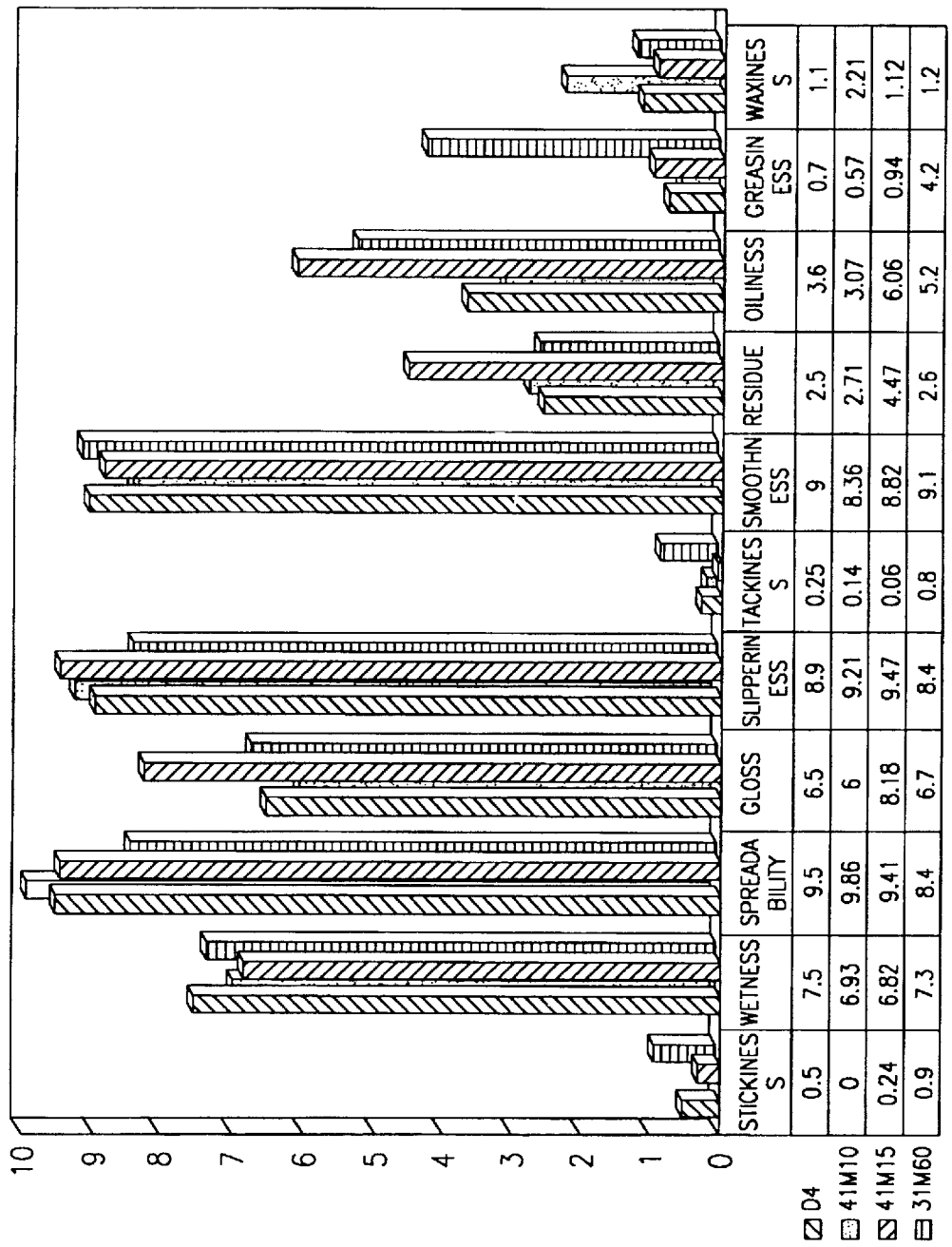
FIG. 1 is a chart showing a comparison of sensory profiles of volatile silicones as described in Example 1 of the present application.
Figure 2:
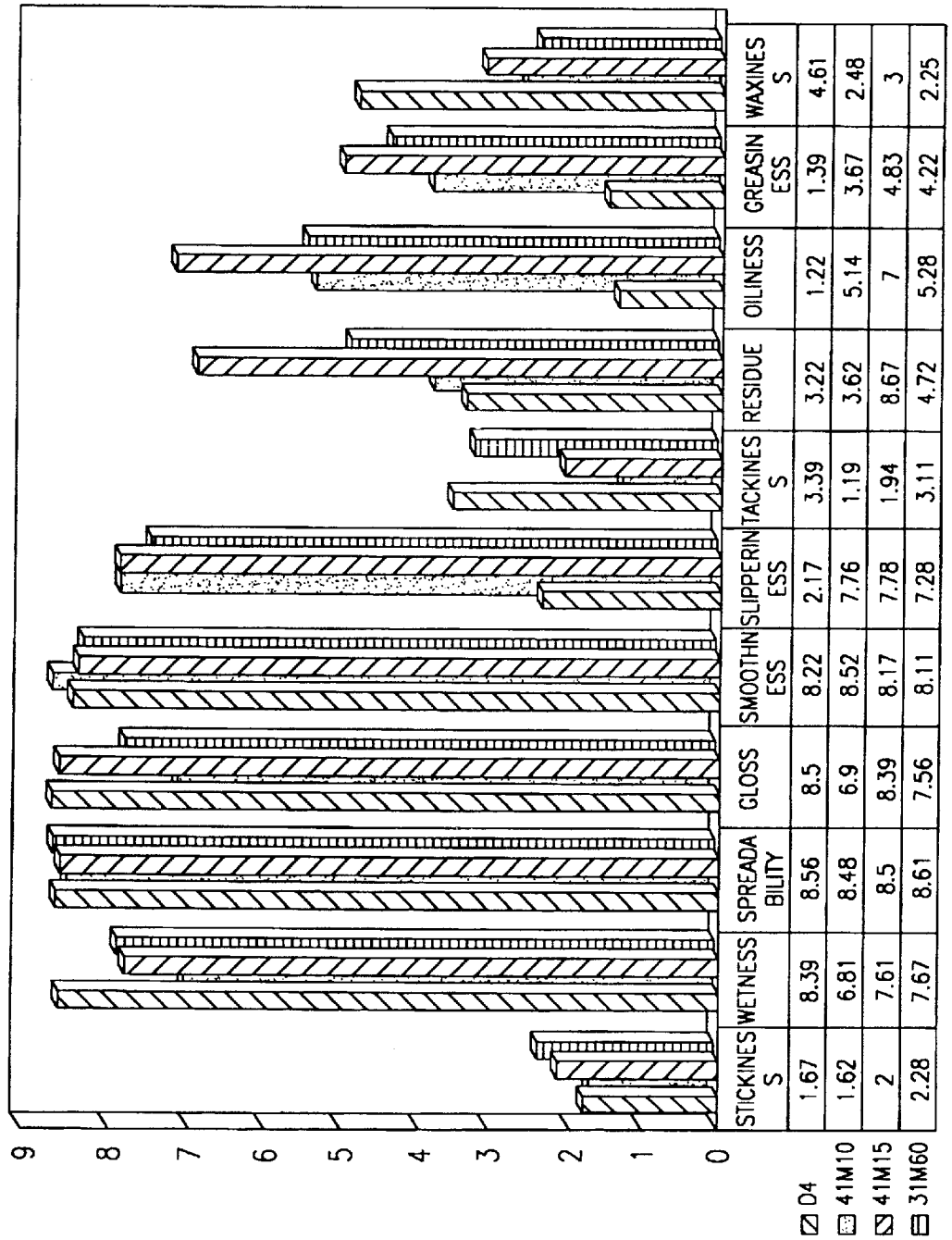
FIG. 2 is a chart showing a comparison of sensory profiles of gelled silicones as described in Example 2 of the present application.

The present invention is directed to improvements in thickened cosmetic formulations which employ a thickening component which does not suffer from the incompatibility problems associated with polydimethylsiloxane gums and elastomers as discussed hereinabove. Further, the present invention is directed to improvements in thickened cosmetic formulations which eliminate potentially toxic ingredients, such as octamethylcyclotetrasiloxane, which are effective in providing an occlusive film on the outer layer of the skin after application, and which maintains or improves upon the aesthetic characteristics of the prior art formulations, during and after application.

To this end the present invention provides a composition having the physical consistency of a gel wherein said composition comprises (a) a volatile or non-volatile silicone-hydrocarbon hybrid fluid, and (b) a gelling agent comprising a non-volatile occlusive silicone-aliphatic hydrocarbon hybrid wax. Aliphatic hydrocarbons are well known to be occlusive, especially as their chain length and molecular weight increase. Exemplary of such materials is petrolatum. On the other hand, silicones are generally not occlusive. Hybridization of these two types of constituents can produce an infinite array of silicone-aliphatic hydrocarbon hybrid materials ranging from volatile non-occlusive fluids to non-volatile high softening point occlusive waxes.

Typical of the volatile non-occlusive silicone-aliphatic hydrocarbon hybrid fluids useful in the practice of the present invention is 3-n-hexyl-1,1,1,3,5,5,5-heptamethyltrisiloxane. This chemical is known to have a volatility similar to that of dimethylcyclosiloxanes such as octamethylcyclotetrasiloxane and decamethylcyclopentasiloxane. Surprisingly, the sensory characteristics of this chemical are virtually identical to those of octamethylcyclotetrasiloxane.

Typical of the non-volatile occlusive high softening point waxes useful in the practice of the present invention is the wax Poly (n-C24–28 Alkylmethylsiloxane) dimethylsiloxane, referred to as C24–28 Alkyl Dimethicone by INCI nomenclature as used in the cosmetic industry. This wax has a softening point of 65 degrees Centigrade and has a hard consistency at room temperature such that it cannot be spread onto the skin to form a continuous film under ambient conditions.

In a preferred embodiment a mixture of 10% w/w C24–28 Alkyl Dimethicone wax and 90% w/w 3-n-hexylheptamethyltrisiloxane is prepared and heated above the softening point of the wax to produce a clear solution. On cooling of the solution to ambient temperature a gel is formed. In spite of the high softening point of the wax alone, this gel has silicone-like aesthetic characteristics and can be readily spread on the skin. As the volatile organosilicone evaporates and adsorbs into the upper layers of the stratum corneum a film of the C24–28 Alkyl Dimethicone wax is left on the surface of the stratum corneum which also has silicone-like aesthetic characteristics in spite of its 70% hydrocarbon content.

It has been found that a range of Poly (alkylmethylsiloxane)dimethylsiloxane copolymers with a hydrocarbon content of at least 60%, an average molecular weight of about 2000 or above, and a softening point of about 50° C. or above will gel volatile fluids of many kinds including, dimethylsilicones, silicone-aliphatic hydrocarbon hybrids, and hydrocarbons at as low as 5% w/w.

Based upon this finding, it is now possible to prepare cosmetic formulations which do not run on the skin, which possess no dimethylcyclosiloxanes, which have dimethylsilicone-like aesthetically pleasing characteristics during application, and which form occlusive films which again are aesthetically pleasing in accordance with the present invention. Furthermore, the difficulty of using dimethylsilicone gums to thicken cosmetic formulations can be avoided. Other cosmetic ingredients, both organic and organosilicone, both inactive and active, can be readily formulated on a uniform basis into these gels.

DETAILED DESCRIPTION OF THE INVENTION

The present invention provides a composition having the physical consistency of a gel wherein said composition comprises (a) a volatile or non-volatile silicone-hydrocarbon hybrid fluid, and (b) a gelling agent comprising a non-volatile occlusive silicone-aliphatic hydrocarbon hybrid wax.

Volatile non-occlusive silicone-aliphatic hydrocarbon hybrid fluids useful in the practice of the present invention are any of those known to those skilled in the art. Preferred are fluids having the general formulae:

$(R_3SiO)_2MeSiR^1$ $(R_3SiO)_3SiR^1$ wherein each R is independently the same or different monovalent straight or branched chain alkyl group having from 1 to about 3 carbon atoms, and $R^1$ is a monovalent straight or branched chain alkyl group having from 6 to about 18 carbon atoms or is phenyl. These are prepared by methods known to those skilled in the art.

Preferred volatile or non-volatile silicone-hydrocarbon hybrid fluids of the present invention are those with sensory characteristics similar to those of octamethylcyclotetrasiloxane, which include 3-n-hexyl-1,1,1,3,5,5,5-heptamethyltrisiloxane, 3-n-octyl-1,1,1,3,5,5,5-heptamethyltrisiloxane, n-hexyltris(trimethylsiloxy)silane, phenyltris(trimethylsiloxy)silane and n-octyltris(trimethylsiloxy)silane. Other useful fluids are those such as, but not limited to 3-n-dodecyl-1,1,1,3,5,5,5-heptamethyltrisiloxane and 3-n-octadecyl-1,1,1,3,5,5,5-heptamethyltrisiloxane. Of course mixtures of any of the fluids may be employed in the practice of the present invention. In preferred embodiments, the fluids employed are at least 99% pure.

The second component of the compositions of the present invention comprises non-volatile occlusive silicone-aliphatic hydrocarbon hybrid waxes. These can be prepared according to methods known to those skilled in the art. Particularly useful in the practice of the present invention are poly(n-alkylmethylsiloxane)dimethylsiloxanes with n-alkyl substitution of an average of 22 carbon atom or above, with an average of more than 2 alkyl groups per molecule, with hydrocarbon contents of at least 60% and with average molecular weights of at least 2000 or more. Examples of waxes preferred for use in accordance with the present invention are random copolymers of the following formula:

$Me_3SiO(RMeSiO)_x(Me_2SiO)_ySiMe_3$ wherein R is an aliphatic hydrocarbon substituent with at least an average of a 22 carbon atom chain, x is at least an average of more than 2, and y is at least 1. Specific examples include R=$C_{20}$–$C_{24}$ and $C_{24}$–$C_{28}$, x=5 and y=3.

The above-described volatile fluids, alone or in any combination, can be gelled with as little as 5% w/w, and up to about 40% or more w/w of any of the above poly(n-alkylmethylsiloxane)dimethylsiloxane waxes. In some embodiments from about 10% to about 20% w/w of wax is employed.

The gels can also be formulated into cosmetic formulation with the addition of other cosmetic ingredients known to those skilled in the art including non-volatile silicone-aliphatic hydrocarbon hybrid fluids, and organic materials such as long chain aliphatic hydrocarbons and esters. Active ingredients such as stearoxytrimethylsilane can be readily formulated into these mixtures. Other cosmetic additives including perfumes, antiperspirant, a humectant, an insect repellent, an odorant, a deodorant, an emollient, an antiseptic, a sunscreen, a cleansing agent, a suitable pharmaceutical, a pigment, a biocide and mixtures of any of the foregoing may also be added.

DESCRIPTION OF THE PREFERRED EMBODIMENTS

The following examples illustrate the present invention. They are not to be construed to limit the scope of the appended claims in any matter whatsoever.

EXAMPLE 1

Following the protocol of ASTM method E 1490–92 entitled "Sensory Evaluation of Materials and Products," a Sensory Panel composed of 24 volunteers was established and trained using reference anchors. Sensory profiles of commercially available silicone products used in the cosmetic industry were determined by this trained panel and shown to match (within experimental error) the published profiles of these products.

Sensory profiles were determined for the following compounds: octamethylcyclotetrasiloxane (D4), 3-n-hexyl-1,1,1,3,5,5,5-heptamethyltrisiloxane (41M10), 3-n-octyl-1,1,1,3,5,5,5-heptamethytrisiloxane (41M15), and n-octyltris-(trimethylsiloxy)silane (31M60). The averaged values for each sensory parameter obtained by the sensory panel are shown and plotted on Chart 1. It may be concluded from these data that the sensory profiles of these materials are very similar.

EXAMPLE 2

Each of the volatile fluids identified in EXAMPLE 1 was gelled using $C_{24}$–$C_{28}$ Alkyl Dimethicone wax. This was accomplished in each case by adding 5 g. of $C_{24}$–$C_{28}$ Alkyl Dimethicone wax to 45 g. of each of the volatile fluids D4, 41M10, 41M15, and 31M60 and then heating the mixtures to approximately 70° C. Clear solutions of the molten wax in the volatile fluids were then allowed to cool back to room temperature. In each case a rigid, non-flowing gel was formed. The sensory characteristics of each of these gels was then determined by the Sensory Panel. The averaged values for each parameter obtained by the sensory panel are shown and plotted on Chart 2.

EXAMPLE 3

In the same manner as described in EXAMPLE 2, 50 g. molten solutions of $C_{24}$–$C_{28}$ Alkyl Dimethicone wax (41M80) in the volatile silicone-aliphatic hydrocarbon fluid 41M10 were prepared at concentrations of 2.5%, 3.5%, 5%, 10% and 20% wax. On cooling to ambient temperature the volatile fluid was completely gelled in all of the samples with 5% wax or more. The samples with 2.5% and 3.5% wax were not fully gelled.

EXAMPLE 4

In the same manner as described in EXAMPLE 2, molten 50 g. solutions of $C_{20}$–$C_{24}$ Alkyl Dimethicone and $C_{24}$–$C_{28}$ Alkyl Dimethicone waxes in the volatile fluid 41M10 were prepared at concentrations of 5% and 10% wax. On cooling to ambient temperature the volatile fluid was completely gelled in all 4 samples.

EXAMPLE 5

In the same manner as described in EXAMPLE 2, a molten solution of 5 g. of $C_{24}$–$C_{28}$ Alkyl Methicone wax, (3-n-($C_{24}$–$C_{28}$) Alkyl-1,1,1,3,5,5,5-heptamethyltrisiloxane), in 45 g. of 41M10 fluid was prepared at 70° C. On cooling to room temperature, this solution showed no indication of gellation.

EXAMPLE 6

In the same manner as described in EXAMPLE 2, a molten solution of 5 g. of $C_{24}$–$C_{28}$ Alkyl Dimethicone (41M80) in 45 g. of 50 cs. mineral oil was prepared at 70° C. On cooling to ambient temperature, the mineral oil was completely gelled to a non-flowing substance.

EXAMPLE 7

In the same manner as described in EXAMPLE 2, the following solutions were prepared at approximately 70° C. and then allowed to cool to ambient temperature. In all cases the mixtures were fully gelled.

(a) 5 g. 41M80 wax, 5 g. $C_{24}$–$C_{28}$ Alkylheptamethyltrisiloxane wax, and 40 g. 41M10 volatile fluid.

(b) 5 g. 41M80 wax, 5 g. 3-n-Stearylheptamethyltrisiloxane non-volatile fluid, and 40 g. 41M10 volatile fluid.

(c) 5 g. 41M80 wax, 5 g. of Stearoxytrimethylsilane, and 40 g. 41M10 volatile fluid.

(d) 5 g. 41M80 wax, and 45 g. Phenyltris(trimethylsiloxy) silane.

(e) 1 g. Dow Corning AMS-C30 wax and 19 g. 41M10 volatile fluid.

Variations of the present invention will suggest themselves to those skilled in the art in light of the above detailed description. For example, a mixture of any combination of volatile silicones described above could be gelled to generate a gel with a sensory profile unlike any of the profiles described above. Other volatile silicones including other cyclosiloxanes, such as decamethylcyclopentasiloxane, or phenyl containing siloxanes may be gelled in the same manner as described above.

The above-referenced patents and publications are hereby incorporated by reference in their entirety.

What is claimed is:

1. A composition having the physical consistency of a gel wherein said composition comprises (a) a volatile or non-volatile silicone-hydrocarbon hybrid fluid comprising a compound of the general formula $$(R_3SiO)_2MeSiR^1$$

$$(R_3SiO)_3SiR^1$$

wherein Me is methyl, each R is independently the same or different monovalent straight or branched chain alkyl group having from 1 to about 3 carbon atoms, and $R^1$ is a monovalent straight or branched chain alkyl group having from 6 to about 18 carbon atoms or phenyl, and (b) at least about 5% w/w of a gelling agent consisting essentially of a non-volatile occlusive silicone-aliphatic hydrocarbon hybrid wax.

2. A composition as defined in claim 1 wherein said components (a) and (b) are known either directly or by inference with other related materials to be safe for human contact or ingestion.

3. A composition as defined in claim 1 wherein said volatile silicone-hydrocarbon hybrid fluid (a) is selected from the group consisting of 3-n-hexyl-1,1,1,3,5,5,5,-heptamethyltrisiloxane, 3-n-octyl-1,1,1,3,5,5,5-heptamethyltrisiloxane, n-hexyltris(trimethylsiloxy)silane, phenyltris(trimethylsiloxy)silane, n-octyltris (trimethylsiloxy)silane and mixtures of any of the foregoing.

4. A composition as defined in claim 1 wherein said volatile silicone-hydrocarbon hybrid fluid (a) is at least about 99% pure.

5. A composition as defined in claim 1 wherein said non-volatile silicone-hydrocarbon hybrid fluid is selected from the group consisting of 3-n-dodecyl-1,1,1,3,5,5,5,-heptamethyltrisiloxane, 3-n-octadecyl-1,1,1,3,5,5,5-heptamethyltrisiloxane and mixtures thereof.

6. A composition as defined in claim 3 wherein said non-volatile silicone-hydrocarbon hybrid wax (b) comprises a polymer of the general formula $$R_3SiO(R^1MeSiO)_x(R_2SiO)_ySiR_3$$

wherein Me is methyl, each R is independently the same or different monovalent straight or branched chain alkyl group having from 1 to about 3 carbon atoms, $R^1$ is a monovalent straight or branched chain alkyl group having from an average of about 22 to an average of about 28 carbon atoms, x is an average of more than 2, y is 1 or more, and the molecular weight of the polymer is about 2000 or more.

7. A composition as defined in claim 3 wherein said non-volatile silicone-hydrocarbon hybrid wax (b) comprises a polymer of the general formula $$R_3SiO(R^1MeSiO)_xSiR_3$$

wherein Me is methyl, each R is independently the same or different monovalent straight or branched chain alkyl group having from 1 to about 3 carbon atoms, $R^1$ is a monovalent straight or branched chain alkyl group having an average of about 22 carbon atoms or more, x is an average of more than 2, and the molecular weight of the polymer is about 2000 or more.

8. A composition as defined in claim 6 wherein said non-volatile silicone-hydrocarbon hybrid wax is selected from $Me_3SiO(C_{20}$–$C_{24}alkylMeSiO)_5(Me_2SiO)_3SiMe_3$, and $Me_3SiO(C_{24}$–$C_{28}AlkylMeSiO)_5(Me_2SiO)_3SiMe_3$ waxes and mixtures of the foregoing.

9. A composition as defined in claim 1 wherein said non-volatile silicone-hydrocarbon wax is present in an amount ranging from about 5% to about 40% (w/w).

10. A composition as defined in claim 1 wherein said non-volatile silicone-hydrocarbon hybrid was is present in an amount ranging from about 10% to about 20% (w/w).

11. A composition as defined in claim 1 further comprising cosmetic additives.

12. A composition as defined in claim 11 wherein said cosmetic additives comprises stearoxytrimethylsilane.

13. A method of treating dry skin comprising delivering to the stratum corneum an effective amount of a composition as defined in claim 1.

* * * * *